United States Patent [19]

Arai

[11] Patent Number: 4,705,023
[45] Date of Patent: Nov. 10, 1987

[54] ENDOSCOPE HAVING ROTATABLE CLAMP INSERTING SECTION

[75] Inventor: Keiichi Arai, Tokyo, Japan
[73] Assignee: Olympus Optical Co., Ltd., Tokyo, Japan
[21] Appl. No.: 863,235
[22] Filed: May 14, 1986

[30] Foreign Application Priority Data

May 20, 1985 [JP]  Japan .................. 60-107735

[51] Int. Cl.⁴ .................................................. A61B 1/00
[52] U.S. Cl. .................................................. 128/4
[58] Field of Search ........................... 128/4, 6, 7, 3, 5

[56] References Cited

U.S. PATENT DOCUMENTS

| 1,127,948 | 2/1915 | Wappler | 128/7 |
| 4,439,030 | 3/1984 | Ueda | 128/4 X |
| 4,607,619 | 8/1986 | Seike et al. | 128/4 |

FOREIGN PATENT DOCUMENTS 2946372 12/1982 Fed. Rep. of Germany .
3206381 9/1983 Fed. Rep. of Germany .
56-68501 10/1981 Japan .

Primary Examiner—William H. Grieb

[57] ABSTRACT

An endoscope comprises a tubular operating section, a clamp inserting section provided on the operating section, an operating tool being inserted into the patient's body cavity through the clamp inserting section, and a channel tube having one end connected to the clamp inserting section and extending through the clamp inserting section into an inserting section. The clamp inserting section is rotatable in the circumferential directions of the operating section by an angle less than 360°.

9 Claims, 9 Drawing Figures

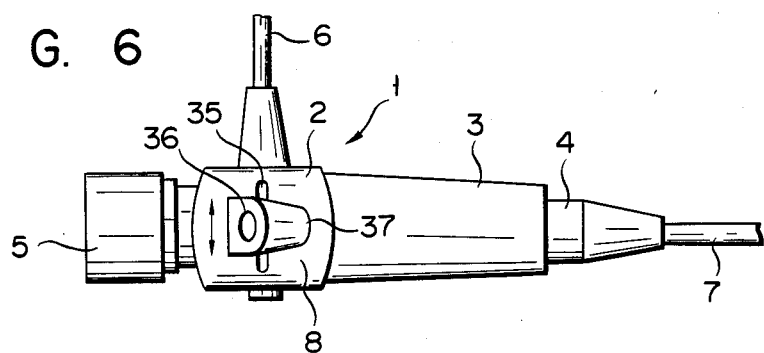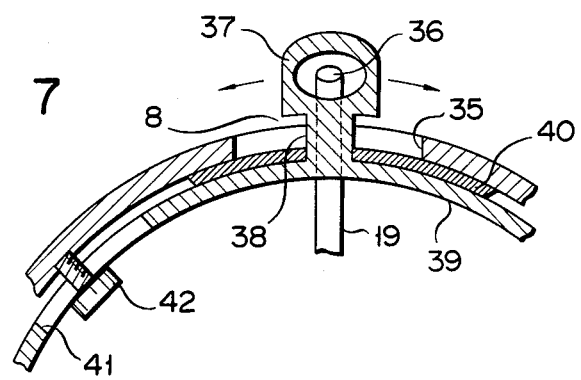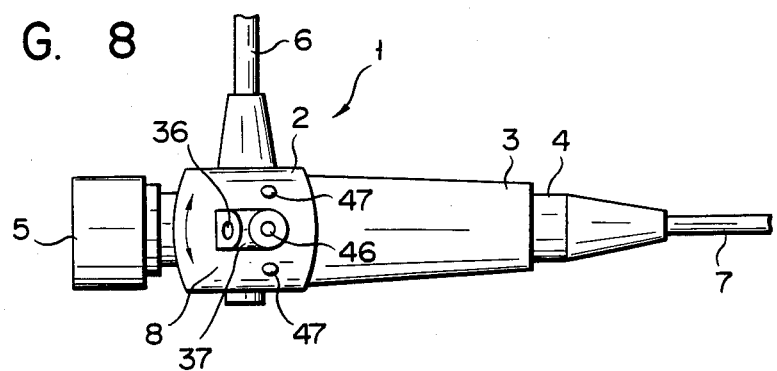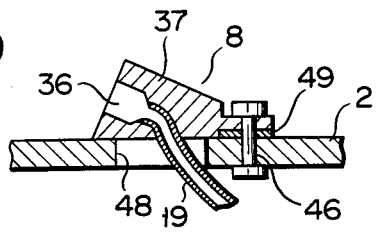

ENDOSCOPE HAVING ROTATABLE CLAMP INSERTING SECTION

BACKGROUND OF THE INVENTION

This invention relates to endoscopes with an operating section provided with a clamp inserting section.

A usual endoscope has a channel for guiding a clamp or like operation tool into the patient's body. The channel has one end open at the end of an inserting section of the endoscope, and the other end open at a clamp inserting section provided on an operating section. The operation tool is guided from the clamp inserting section through the channel into the patient's body.

With this prior art endoscope, the clamp inserting section is open toward the center of the operating section. Therefore, when the operator inserts the operation tool into the clamp inserting section from the left side of the operating section with the left hand, while gripping the section with the right hand, or he or she when inserts the tool from the right side of the section with the right hand, while gripping the section with the left hand, he or she must bend the hand inserting the tool unnaturally to insert the tool into the clamp inserting section. The tool, therefore, cannot be efficiently inserted, and the operator is tired. In another aspect, the operating section is sometimes rotated to direct the end of the inserting section to a different position during observation of the patient's body cavity. In this case, the clamp inserting section is also rotated with the operating section. In consequence, the opening of the clamp inserting section is further deviated, making it further difficult to insert the operation tool.

SUMMARY OF THE INVENTION

An object of the invention is to provide an endoscope, with which the clamp inserting section can be orientated to allow an easy insertion of the operation tool.

BRIEF DESCRIPTION OF THE DRAWINGS

FIG. 6 is a side view showing part of a second embodiment of the endoscope according to the invention;

FIG. 7 is a transversal, sectional view showing part of the endoscope shown in FIG. 6;

FIG. 8 is a side view showing part of a third embodiment of the endoscope according to the invention; and FIG. 9 is a transversal, sectional view showing part of the endoscope shown in FIG. 8.

DETAILED DESCRIPTION OF THE PREFERRED EMBODIMENTS

Now, some preferred embodiments of the endoscope according to the invention will be described with reference to the accompanying drawings.

Figure 1:
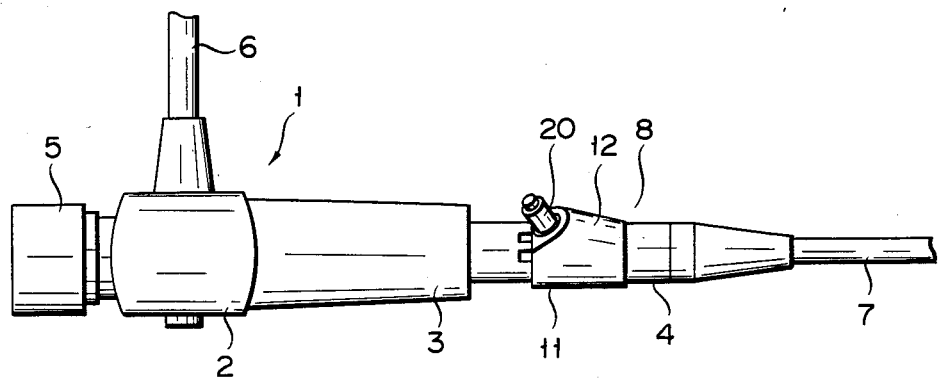
FIG. 1 is a side view showing part of a first embodiment of the endoscope according to the invention.
Figure 3:
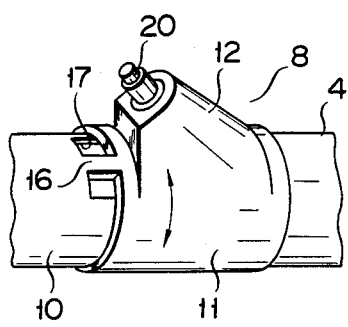
FIG. 3 is a perspective view showing a clamp inserting section of the same endoscope.
Figure 2:
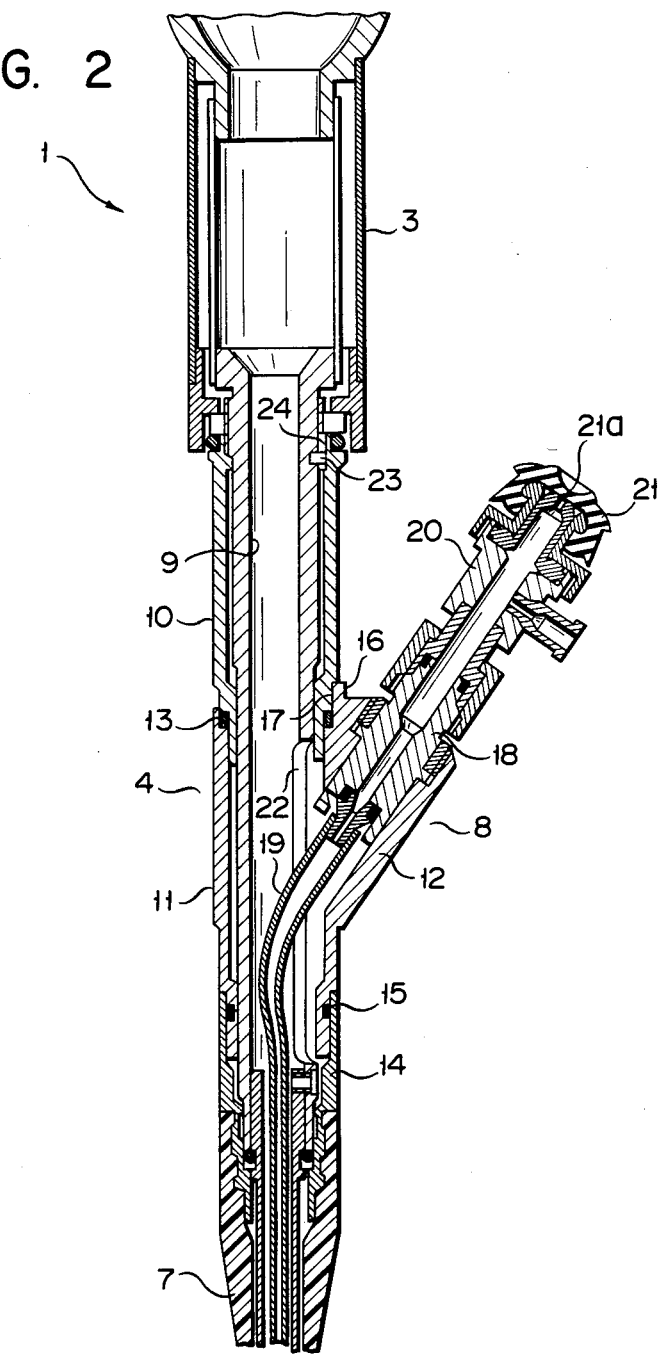
FIG. 2 is a longitudinal, sectional view showing part of the same endoscope.

FIGS. 1 to 3 show a first embodiment. This endoscope has operating section 1 for performing various operations outside the patient's body. Operating section 1 includes main body section 2, grip section 3 extending from an end of main body section 2, and end section 4 extending from an end of grip section 3. Main body section 2 has ocular section 5 provided at the other end, i.e., stem. Light guide cable 6 is connected to the periphery of main body section 1. The stem of an inserting section 7 is connected to the free end of end section 4. A conventional distal end (not shown) is connected to the free end of inserting section 7. Clamp inserting section 8 is mounted on end section 4 and can move around section 4, as will be described later in detail.

As shown in FIG. 2, end section 4 has tubular support 9 having a stem secured to grip section 3. Tubular cover 10 is coaxially provided on the outer periphery of a stem portion of tubular support 9. Clamp inserting section 8 is mounted on an end portion of end section 4 such that it can be rotated about the axis of operating section 1, i.e., center line of tubular support 9. Section 8 has support section 11 and branch section 12 outwardly extending from section 11 at an angle. Support section 11 is coaxially and rotatably mounted on the outer periphery of tubular support 9. First O-ring 13 made of an elastic material such as rubber is provided between the inner periphery of the rear end of support section 11 and the outer periphery of the front end of cover 10. First O-ring 13 ensures liquid tightness between support section 11 and cover 10, and it also acts as a frictional engagement member constituting holder means. Second O-ring 15 made of an elastic material such as rubber is provided between the outer periphery of the front end of support section 11 and tubular retainer cover 14 covering the same outer periphery. Second O-ring 15 ensures liquid tightness between support section 11 and retainer cover 14, and it also acts as a frictional engagement member. Clamp inserting section 8 is held at a given position against free rotation by the frictional resistances offered by first and second O-rings 13 and 15. Support section 11 has rearward extension extending 16 from part of the rear end. Rearward extension 16 is received for movement in circumferential directions in guide groove 17, which is cut in the outer periphery of cover 10 and extend circumferentially for a predetermined angle of less than 360°, for example 180° or less. Clamp inserting section 8 can thus rotate by an angle to move rearward extension 16 along guide groove 17, i.e., by the angle subtended by guide groove 17.

First inlet member 18 is secured to branch section 12 of clamp inserting section 8 with its free end portion inserted in branch section 12. The rear end of channel tube 19, which is a flexible tube forming a channel, is connected to the free end of first inlet member 18. Second inlet member 20 is connected to the rear end of first inlet member 18. The open end of second inlet member 20 is closed by clamp plug 21, which is made of an elastic material, e.g., rubber, and has a central notch 21a. A clamp or like operation tool, not shown, can be inserted into channel tube 19 by forcibly opening the notch of clamp plug 21. Channel tube 19 is led into operating section 1 through opening 22 which is formed in the peripheral wall of tubular support 9 and extends circumferentially to subtend a predetermined angle. Channel tube 19 extends through operating section 1 and inserting section 7, and has an open end open at the free end of inserting section 7. Thus, the operation tool inserted into channel tube 9 can be led into the patient's body cavity through the free end of inserting section 7.

Tubular support 9 has a lock pin 23 formed on the outer periphery near the rear end. Lock pin 23 is engaged in engagement groove 24 formed in the inner periphery of the rear end of cover 10 to prevent relative rotation of tubular support 9 and cover 10. Opening 22 has a sufficient circumferential dimension, i.e., subtends a sufficient angle, so that channel tube 19 will not touch the edges of opening 22 when clamp inserting section 8 is rotated.

With the endoscope having the above construction, when inserting the operation tool with the right hand, the clamp inserting section 8 is turned to the right while holding grip section 3 with the left hand. Clamp plug 21 provided on second inlet member 20 thus is brought to a position on the right side of the center of operating section 1. In this status, the operator can insert the tool through clamp plug 21 into channel tube 19, without unnaturally bending the right hand. When inserting the operation tool with the left hand, clamp inserting section 8 is turned in the opposite direction to bring clamp plug 21 to a position on the left side of the center of operating section 1. In this case, the operation tool can be easily inserted through clamp plug 21 into channel tube 19 with the left hand. Since rearward extension 16 of support section 11 of clamp inserting section 8 is engaged in guide groove 17, the rotation of clamp inserting section 8 is restricted according to the circumferential angle subtended by guide groove 17. Therefore, there is no possibility of excessively turning clamp inserting section 8 in one direction to cause twisting of channel tube 19 or make it impossible to insert the operation tool. Further, clamp inserting section 8 can be held at a desired rotational position by the frictional resistances offered by first and second O-rings 13 and 15. Thus, clamp inserting section 8 can be positioned to be most suitable for insertion within its rotational angle defined by guide groove 17.

Figure 4:
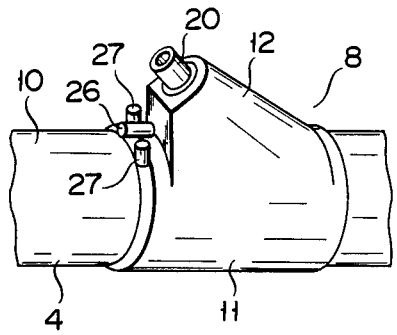
FIG. 4 is a view similar to FIG. 3 but showing a modification of the clamp inserting section.
Figure 5:
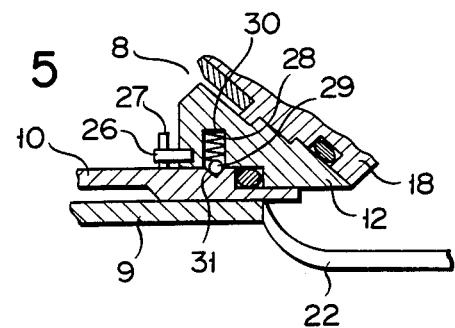
FIG. 5 is a longitudinal, sectional view showing the clamp inserting section shown in FIG. 4.

FIGS. 4 and 5 show a second embodiment of the invention. This embodiment is different from the preceding first embodiment in the structure of defining the rotational angle of clamp inserting section 8. More specifically, branch section 12 of clamp inserting section 8 has engagement pin 26 extending from the rear end, while on the outer periphery of the free end of cover 10 there are provided with a pair of outwardly extending stopper pins 27 circumferentially spaced apart a predetermined distance. The rotation of clamp inserting section 8 is restricted by the engagement of engagement pin 26 with stopper pins 27. Further, in this embodiment branch section 12 is formed with recess or accommodation space 28 open on the inner periphery in frictional contact with the outer periphery of cover 10. Spring 28 and ball 29 are accommodated in accommodation space 30 such that ball 29 is outwardly spring biased. The outer periphery of cover 10, on the other hand, is formed with a plurality of recesses 31 circumferentially spaced at a predetermined interval. Ball 29 thus can be click engaged and disengaged with respect to recesses 31 owing to the spring force of spring 28. This function assists the frictional resistances offered by first and second O-rings 13 and 15 to reliably hold clamp inserting section 8 at a desired angular position.

FIGS. 6 and 7 show a third embodiment of the invention. This embodiment is different from the previous first embodiment in that clamp inserting section 8 is mounted on main body section 2 of operating section. More specifically, main body section 2 has a slide guide slat 35 formed circumferentially in the peripheral wall. On the other hand, clamp inserting section 8 has slider section 39 and head section 37 integral therewith via constricted section 38. Head section 37 has see-through hole 36 which communicates with channel tube 19. Slider section 39 is provided in main body section 2 with packing 40 provided as a frictional member between it and inner periphery of main body section 2, and constricted section 38 slidably penetrates side guide slat 35. Slider section 19 has circumferential slot 41 extending in the same direction as slide guide slot 35. Engaged in slot 41 is stopper pin 42, which projects from the inner periphery of main body section 2 and has a head having a greater diameter than the width of slot 41. Clamp inserting section 8 is thus slidable along side guide slot 35. The range of sliding is defined by the engagement of stopper pin 42 with each end of slot 41. Clamp inserting section 8 can be held at a desired position by the frictional resistance offered by packing 40.

FIGS. 8 and 9 show a fourth embodiment of the invention. This embodiment is the same as the preceding third embodiment insofar as clamp inserting section is provided on main body section 2 but is different from the third embodiment in the structure of mounting the clamp inserting section. More specifically, in this embodiment clamp inserting section 8 is mounted on a flat surface of main body section 2. It is mounted on main body section 2 by pin 46, about which it can be rotated. Its rotational angle is defined by a pair of stopper pins 47 projecting from main body section 2. Channel tube 19 connected to see-through hole 36 of clamp inserting section 8 is led through a see-through hole 48 formed in the peripheral wall of main body section 2. Packing 49 is provided as a frictional member between clamp inserting section 8 and main body section 2, so that clamp inserting section 8 can be held at a desired rotational position. With this structure, by turning clamp inserting section 8 about pin 46 the orientation of see-through hole 36 can be varied so that the operation tool can be easily inserted as in the previous first embodiment.

Although not shown, according to the invention clamp inserting section 8 may be provided between main body section 2 and ocular section 5 or any other desired portion in operating section 1.

As has been described in the foregoing, according to the invention the clamp inserting section is mounted on the operating section for movement relative thereto, for instance in the circumferential direction, so that it can be brought to an orientation suited for easily inserting the operation tool. The operation tool thus can be inserted easily and quickly.

What is claimed is:

1. An endoscope comprising:
   a tubular operating section having a longitudinal axis;
   an inserting section connected to said operating section and inserted into the patient's body cavity;
   a clamp inserting section provided on said operating section, an operating tool being inserted into the patient's body cavity through said clamp inserting section; and
   a channel tube having one end connected to said clamp inserting section and extending through said clamp inserting section into said inserting section;
   said operating section including means for supporting said clamp inserting section such that said clamp inserting section is rotatable in the circumferential directions of said operating section by an angle less than 360°.

2. The endoscope according to claim 1, wherein said clamp inserting section has a portion projecting at an angle with respect to said longitudinal axis of said operating section, said angle being held constant while said clamp inserting member is rotated with respect to said operating section.

3. The endoscope according to claim 2, wherein said support means includes holder means for holding said clamp inserting section at a predetermined position.

4. The endoscope according to claim 3, wherein said holding means includes a tubular support coaxial with said longitudinal axis, and said clamp inserting section includes a support section mounted on said tubular support for rotation about said longitudinal axis, a branch section extending from said support section at a predetermined angle thereto, and an inlet member provided on the free end of said branch section.

5. The endoscope according to claim 4, wherein said support means includes a recess formed in said operating section and extending circumferentially to subtend a predetermined angle and an engagement projection provided on said clamp inserting section and engaged in said recess for movement in the circumferential directions, the movement of said clamp inserting section being restricted according to the range of movement of said engagement projection.

6. The endoscope according to claim 5, wherein said holding means includes an O-ring made of an elastic material and provided between said support section and tubular support.

7. The endoscope according to claim 4, wherein said support means includes a pair of pins spaced apart in the circumferential direction to subtend a predetermined angle and an engagement projection provided on said clamp inserting section, between said pair pins, the movement of said clamp inserting section being restricted according to the range of movement of said engagement projection between said pair pins.

8. The endoscope according to claim 7, wherein said holding means includes a frictional member provided between and in frictional engagement with said support section and tubular support.

9. The endoscope according to claim 7, wherein said holding means includes a click mechanism provided between said support section and tubular support.

* * * * *